United States Patent [19]

Levine et al.

[11] 4,189,534

[45] Feb. 19, 1980

[54] CELL CULTURE MICROCARRIERS

[75] Inventors: David W. Levine, Somerville; William G. Thilly, Cambridge; Daniel I. C. Wang, Belmont, all of Mass.; Jason S. Wong, Toledo, Ohio

[73] Assignee: Massachusetts Institute of Technology, Cambridge, Mass.

[21] Appl. No.: 842,696

[22] Filed: Oct. 17, 1977

Related U.S. Application Data

[63] Continuation-in-part of Ser. No. 740,993, Nov. 11, 1976, abandoned.

[51] Int. Cl.$^2$ .......................... C12B 3/00; C12K 9/00
[52] U.S. Cl. ..................................................... 435/2
[58] Field of Search ........................................ 195/1.8

[56] References Cited

U.S. PATENT DOCUMENTS

| | | | |
|---|---|---|---|
| 3,717,551 | 2/1973 | Bizzini et al. | 195/1.7 |
| 3,904,480 | 9/1975 | Hall et al. | 195/1.7 |
| 3,910,819 | 10/1975 | Rembaum et al. | 195/1.8 |
| 4,036,693 | 7/1977 | Levine et al. | 195/1.8 |

FOREIGN PATENT DOCUMENTS 651507 10/1962 Canada.

OTHER PUBLICATIONS

Horng—Primary Culture of Mammalian Cells on Microcarrier Surface, PHD Thesis, State University of N.Y., Buffalo 1975.

Levine et al.—Proceedings from 1st International Cell Culture Congress (Sep. 21-25, 1975) Birmingham, Alabama.

*Primary Examiner*—Sam Rosen
*Attorney, Agent, or Firm*—Arthur A. Smith, Jr.; David E. Brook

[57] ABSTRACT

Improved cell culture microcarriers, and methods for their production and use, are disclosed herein. These improved microcarriers have positive charge capacities adjusted and/or controlled within a range suitable for good cell growth. One method for producing such improved microcarriers is by treating beads formed from polymers containing pendant hydroxy groups, such as dextran beads, with an aqueous solution of an alkaline material and a chloro- or bromo-substituted tertiary amine under precisely controlled conditions to produce the desired exchange capacity. The resultant positively charged microcarriers have been used in microcarrier cultures to produce outstanding growth of anchorage-dependent cells. Such cells can be harvested, or used for the production of viruses, vaccines, hormones, interferon or other cellular growth by-products.

20 Claims, 2 Drawing Figures

CELL CULTURE MICROCARRIERS

GOVERNMENT SUPPORT

The Government has rights in this invention pursuant to NSF Grant No. BMS 7405676A01 and NIEHS Grant NO. T01 ES 00063.

RELATED APPLICATION

This is a continuation-in-part of Ser. No. 740,993, filed Nov. 11, 1976 now abandoned.

BACKGROUND OF THE INVENTION

1. Field of the Invention

This invention is in the field of biology and more particularly in the field of cell biology.

2. Description of the Prior Art

The ability to grow mammalian cells is important at both the laboratory and industrial levels. At the laboratory level, the limiting factor for cellular or viral research at the sub-cellular level is often the amount of raw material available to be studied. At the industrial level, there is much effort being devoted to the development of pharmaceuticals based on mammalian cell products. These are primarily vaccines for human or animal viruses, but also include human growth hormone and other body hormones and biochemicals for medical applications.

Some mammalian cell types have been adapted for growth in suspension cultures. Examples of such cell types include HeLa (human), BHK (baby hamster kidney) and L cells (mouse). Such cells, in general, have non-normal genetic complements, i.e., too many or too few chromosomes or abnormal chromosomes. Often, these cells will produce a tumor upon injection into an animal of the appropriate species.

Other mammalian cell types have not been adapted for growth in suspension culture to date, and will grow only if they can become attached to an appropriate surface. Such cell types are generally termed "anchorage-dependent" and include 3T3 mouse fibroblasts, mouse bone marrow epithelial cells; Murine leukemia virus-producing strains of mouse fibroblasts, primary and secondary chick fibroblasts; WI-38 human fibroblast cells; and, normal human embryo lung fibroblast cells (HEL299, ATCC #CCL137). Some anchorage-dependent cells have been grown which are tumor causing but others were grown and found to be non-tumor causing. Also, some anchorage-dependent cells, such as WI-38 and HEL299, can be grown which are genetically normal.

Whereas considerable progress has been made in large scale mammalian cell propagation using cell lines capable of growth in suspension culture, progress has been very limited for large scale propagation of anchorage-dependent mammalian cells. Previous operational techniques employed for large scale propagation of anchorage-dependent cells were based on linear expansion of small scale processes. Cell culture plants utilized a large number of low yield batch reactors, in the forms of dishes, prescription bottles, roller tubes and roller bottles. Each of these was a discrete unit or isolated batch reactor requiring individual environmental controls. These controls, however, were of the most primitive type due to economic considerations. Variation in nutrients was corrected by a medium change, an operation requiring two steps, i.e., medium removal and medium addition. Since it was not uncommon for a moderately sized facility to operate hundreds of these batch reactors at a time, even a single change of medium required hundreds of operations, all of which had to be performed accurately, and under exacting sterile conditions. Any multiple step operation, such as cell transfer or harvest, compounded the problem accordingly. Thus, costs of equipment, space and manpower were great for this type of facility.

There are alternative methods to linear scale-up from small batch cultures which have been proposed. Among such alternatives which have been reported in the literature are plastic bags, stacked plates, spiral films, glass bead propagators, artificial capillaries, and microcarriers. Among these, microcarrier systems offer certain outstanding and unique advantages. For example, great increases in the attainable ratio of growth surface to vessel volume (S/V) can be obtained using microcarriers over both traditional and newly developed alternative techniques. The increase in S/V attainable allows the construction of a single-unit homogeneous or quasi-homogeneous batch or semi-batch propagator for high volumetric productivity. Thus, a single stirred tank vessel with simple feedback control for pH and $pO_2$ presents a homogeneous environment for a large number of cells thereby eliminating the necessity for expensive and space consuming, controlled environment incubators. Also, the total number of operations required per unit of cells produced is drastically reduced. In summary, microcarriers seem to offer economies of capital, space and manpower in the production of anchorage-dependent cells, relative to current production methods.

Microcarriers also offer the advantage of environmental continuity since the cells are grown in one controlled environment. Thus, microcarriers provide the potential for growing anchorage-dependent mammalian cells under one set of environmental conditions which can be regulated to provide constant, optimal cell growth.

One of the more promising microcarrier systems to date has been reported by van Wezel and involves the use of diethylaminoethyl (DEAE)-substituted dextran beads in a stirred tank. A. L. van Wezel, "Growth of Cell Strains and Primary Cells on Microcarriers in Homogeneous Culture", *Nature* 216:64 (1967); D. van Hemert, D. G. Kilburn and A. L. van Wezel, "Homogeneous Cultivation of Animal Cells for the Production of Virus and Virus Products", *Biotechnol. Bioeng.* 11:875 (1969); and A. L. van Wezel, *"Microcarrier Cultures of Animal Cells", Tissue Culture, Methods and Applications,* P. F. Kruse and M. K. Patterson, eds., Academic Press, New York, p. 372 (1973). These beads are commercially produced by Pharmacia Fine Chemicals, Inc., Piscataway, N.J., under the tradename DEAE-Sephadex A50, an ion exchange system. Chemically, these beads are formed from a crosslinked dextran matrix having diethylaminoethyl groups covalently bound to the dextran chains. As commercially available, DEAE-Sephadex A50 beads are believed to have a particle size of 40–120μm and a positive charge capacity of about 5.4 meq per gram of dry, crosslinked dextran (ignores weight of attached DEAE moieties). Other anion exchange resins, such as DEAE-Sephadex A25, QAE-Sephadex A50 and QAE-Sephadex A25 were also stated by van Wezel to support cell growth.

The system proposed by van Wezel combines multiple surfaces with movable surfaces and has the potential for innovative cellular manipulations and offers advantages in scale-up and environmental controls. Despite this potential, these suggested techniques have not been significantly exploited because researchers have encountered difficulties in cell production due to certain deleterious effects caused by the beads. Among these are initial cell death among a high percentage of the cell inoculum and inadequate cell growth even for those cells which attach. The reasons for these deleterious effects are not thoroughly understood, although it has been proposed that they may be due to bead toxicity or nutrient adsorption. See van Wezel, A. L. (1967), *Nature* 216: 64–65; van Wezel, A. L. (1973), *Tissue Culture, Methods and Applications*. Kruse, P. R. and Patterson, M. R. (eds.), pp. 372–377, Academic Press, New York; van Hemert, P., Kilburn, D. G., and van Wezel, A. L. (1969), *Biotechnol. Bioeng.* 11: 875–885; Horng, C. and McLimans, W. (1975), *Biotechnol. Bioeng.* 17: 713–732.

It could be that the deleterious effects of these commercially available ion exchange resins are due to their method of manufacture. Certain of these production methods are described for polyhydroxy materials in patents such as: U.S. Pat. Nos. 3,277,025; 3,275,576; 3,042,667 and 3,208,994 all to Flodin et al. Whatever the reason, however, the presently commercially available materials are simply not sufficient for good cell growth of a wide variety of cell types.

One solution to overcoming some of the deleterious effects encountered in attempts to use such commercially available microcarriers for cell growth is described in U.S. Pat. No. 4,036,693, issued on July 19, 1977 to Levine et al. Therein, a method for treating these commercially available ion exchange resins with macromolecular polyanions, such as carboxymethylcellulose, is proposed. While this method has proven successful, it would clearly be more advantageous if the beads could be manufactured initially to have properties designed for outstanding growth of anchorage-dependent cells.

SUMMARY OF THE INVENTION

It has now been discovered that the charge capacity of microcarriers has to be adjusted and/or controlled within a certain range to result in good growth of a wide variety of anchorage-dependent cell types at reasonable microcarrier concentrations. Based upon this discovery, microcarrier beads have been produced with controlled charge capacities and such beads have been used to obtain good growth of a variety of anchorage-dependent cells. Cells grown using such microcarrier systems can be harvested or used in the production of animal or plant viruses, vaccines, hormones, interferon or other cell growth by-products.

One example of the improved microcarriers is those produced using polymers with pendant hydroxy groups, such as crosslinked dextran beads. These beads can be treated with an aqueous solution of a tertiary or quaternary amine, such as diethylaminoethylchloride:chloride, and an alkaline material, such as sodium hydroxide. The specific charge capacity of the beads is controlled by varying the absolute amounts of the dextran, tertiary amine salt and alkaline material, the ratio of these materials, and/or the time and temperature of treatment.

Microcarriers produced according to this invention can be used in cultures without the high initial cell loss heretofore experienced with commercially available microcarriers. Additionally, attached cells spread and grow to confluence on the beads reaching extremely high cell concentrations in the suspending medium. The concentration of microcarriers in suspension is not limited to very low levels as was customary with the prior art materials, and cell growth appears only to be limited by factors which do not appear to be associated with the microcarriers. Because of this, great increases in the volumetric productivity of cell cultures can be obtained. In short, the potential offered from the use of microcarriers in the growth of cells, and particularly anchorage-dependent cells, can now be realized.

DESCRIPTION OF PREFERRED EMBODIMENTS

Figure 1:
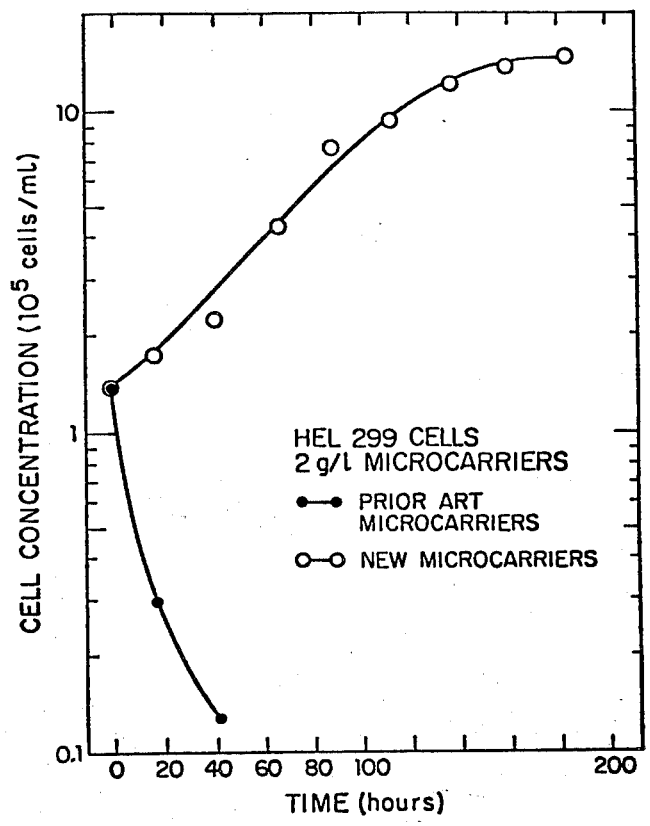
FIG. 1 is a plot graphically illustrating the growth characteristics of normal diploid human embryo lung fibroblast cells (HEL299) at a microcarrier concentration of 2 grams dry, crosslinked dextran/liter for both commercially available DEAE-treated dextran microcarriers and DEAE-treated microcarriers produced according to this invention.

As used herein, the terms "microcarriers", "cell-culture microcarriers" and "cell-growth microcarriers" mean small, discrete particles suitable for cell attachment and growth. Often, although not always, microcarriers are porous beads which are formed from polymers. Usually, cells attach to and grow on the outer surfaces of such beads.

As previously described, it has now been discovered that the amount of charge capacity on cell culture microcarriers must be adjusted and/or controlled to be within a certain range for adequate cell growth at reasonable microcarrier concentrations. Suitable operating and preferred ranges will vary with such factors as the specific cells to be grown, the nature of the microcarriers, the concentration of microcarriers, and other culture parameters including medium composition. In all cases, however, the amount of charge capacity which has been found to be suitable is significantly below the amounts believed to be present on commercially available anion exchange resins previously suggested for microcarrier cell cultures. For example, it is believed that the DEAE-Sephadex A50 beads, suggested by van Wezel, have a charge capacity of about 5.4 meq/gram of dry, untreated (without DEAE), crosslinked dextran. In contradistinction to this relatively high charge capacity, microcarriers have been produced and found suitable for good cell growth according to this invention which have between about 0.1 and about 4.5 meq/gram of dry, untreated microcarriers. Below about 0.1 meq/gram, it is believed that cells would have difficulty attaching to the microcarriers. Above about 4.5 meq/gram, losses of initial cell inoculum take place, and even the surviving cells do not grow well, particularly at relatively high microcarrier concentrations.

For the growth of normal diploid human fibroblasts on crosslinked dextran microcarriers, it has been found that a preferred range of charge capacity supplied by DEAE groups is from about 1.0 to about 2.8 meq/gm of dry, untreated crosslinked dextran. While the preferred range may vary with different cell types or culture conditions, it is believed that the preferred ranges for any given set of conditions will be within the 0.1–4.5 meq/gm range. The preferred and optimum conditions can be determined by a person skilled in the art for any set of conditions by routine experimentation.

It will be recognized, of course, that there are certain deficiencies in attempting to define the charge capacity of microcarriers strictly on a unit weight basis. For example, two beads identical in every way except that they are formed from materials having different densities with the same charge distribution thereon would yield different values for their charge capacity per unit weight. Similarly, two beads having identical charge capacities per unit weight might have quite different charge distributions thereon.

An alternative definition can be made by specifying the range of suitable charges in terms of charge capacity per unit weight of microcarriers in their final functional form. This basis would take into account such factors as the weight of attached DEAE or other positively charged groups, as well as hydration of the beads, etc., whereas the prior definition is based on dry, crosslinked dextran and does not take such factors into account. In an aqueous cell culture medium, the density of microcarriers should be close to 1.0 gram/cc so that the microcarriers can be readily dispersed throughout the culture. Based upon this, it has been determined that the range of suitable charge capacities for microcarriers of this invention defined in this way is from about 0.012 to about 0.25 meq/gram.

The ranges of suitable charge capacities previously specified on a weight basis are valid assuming the microcarriers have a substantially uniform charge distribution throughout their bulk. If the charge distribution is uneven, it might be possible to have suitable microcarriers having charge capacities outside of those ranges. The important criterion is, of course, that the charge capacity be adjusted to and/or controlled at a value sufficient to allow good cell growth on the microcarriers.

Since it may be the charge pattern on the outer surface which is important, it is also desirable to be able to define the suitable charge capacity range in terms of the likely surface pattern. This can be done by assuming that the active portion of the microcarriers represents only the outer surface of the bead to a depth of about 20 angstroms. If it is also assumed that the charged groups in the previously mentioned cases are evenly distributed throughout the beads, the previous ranges can be converted to a charge capacity in this outer shell. Using this approach, the range of charge capacity found suitable is from about 0.012 meq/cm$^3$ to about 0.25 meq/cm$^3$. This approach takes changes in microcarrier volume due to different charge densities into account.

Microcarriers having the required charge capacity can be prepared by treating microcarriers formed from polymers containing pendant hydroxyl groups with an aqueous solution of an alkaline material and a tertiary or quaternary amine. The beads can be initially swollen in an aqueous medium without the other ingredients, or can be simply contacted with an aqueous medium containing the required base and amine. This method of using alkaline materials to catalyze the attachment of positively charged amino groups to hydroxyl-containing polymers is described in Hartmann, U.S. Pat. No. 1,777,970.

Examples of suitable hydroxyl-containing polymers include polysaccharides such as dextran, dextrin, starch, cellulose, polyglucose and substituted derivatives of these. Certain synthetic polymers such as polyvinyl alcohol and hydroxy-substituted acrylates or methacrylates, such as hydroxyethyl methacrylate, are also suitable. Dextran, and especially crosslinked dextran in the form of small spheres or beads, is particularly preferred because it is commercially available, relatively inexpensive, and produces microcarriers which support excellent cell growth.

Any material which is alkaline can be used for the reaction. The alkali metal hydroxides, such as sodium or potassium hydroxide, are, however, the preferred alkaline substances.

Either tertiary or quaternary amines are suitable sources of positively charged groups which can be appended onto the hydroxy-containing polymers. Particularly preferred materials are chloro- or bromo-substituted tertiary amines or salts thereof, such as diethylaminoethylchloride, diethylaminoethylbromide, dimethylaminoethylchloride, dimethylaminoethylbromide, diethylaminomethylchloride, diethylaminomethylbromide, di-(hydroxyethyl)-aminoethylchloride, di-(hydroxyethyl)-aminoethylbromide, di-(hydroxyethyl)-aminomethylchloride, di-(hydroxyethyl)-aminomethylbromide, $\beta$-morfolinoethylethylchloride, $\beta$-morfolinoethylbromide, $\beta$-morfolinomethylchloride, $\beta$-morfolinomethylbromide and salts thereof, for example, the hydrochlorides.

A wide range of reaction temperatures and times may be used. It is preferred to carry out the reactions at temperatures of about between 18° C. and 65° C. However, other temperatures can be used. The reaction kinetics depend to a large extent, of course, upon the reaction temperature and the concentration of reactants. Both the time and temperature do affect the final exchange capacity achieved.

The reason that the charge capacity of the microcarriers is so critical in cell growth is not thoroughly understood. While not wishing to be bound by this theory, it is possible that the charge capacity at the surface causes certain local discontinuities of medium composition which are the major controlling influence in microcarrier culture cell growth. Nevertheless, this is not meant to rule out other possibilities.

There may be certain beads, of course, that will not be suitable for good cell growth even though they have a charge capacity within one of the ranges specified. This may be due to side chains on the moiety supplying the charge capacity which are toxic or otherwise deleterious for cell growth, the presence of adsorbed or absorbed deleterious compositions or compounds, or it may be due to the porosity of the bead or due to other reasons. If such beads are not suitable for cell growth except for the amount of charge capacity, the beads are not considered to be "cell-growth microcarriers."

The invention is further illustrated by the following examples.

EXAMPLE 1

Preparation of Improved Microcarriers

Improved microcarriers can be produced as follows. Dry, uncharged, crosslinked dextran beads are sieved to obtain those of approximately 75 $\mu$m in diameter. One gram of this fraction is added to 10 ml of distilled water and the beads are allowed to swell. An adequate commercial source of dry, crosslinked dextran is Sephadex G-50 from Pharmacia Fine Chemicals, Piscataway, N.J.

An aqueous solution containing 0.01 moles of diethylaminoethylchloride:chloride, twice recrystallized from methylene chloride, and 0.015 moles of sodium hydroxide is formed in a 10 ml volume. This aqueous solution is then added to the swollen dextran bead suspension, which is then agitated vigorously in a shaking water bath for one hour at 60° C. After one hour, the beads are separated from the reaction mixture by filtration on Whatman filter paper No. 595 and washed with 500 ml of distilled water.

Beads made by this procedure contain approximately 2.0 meq of charge capacity per gram of dry, untreated crosslinked dextran. This charge capacity can be characterized by measuring the anion exchange capability of the beads as follows. The bead preparations are washed thoroughly with 0.1 normal HCl to saturate all exchange sites with $Cl^-$ ions. They are then rinsed with $10^{-4}$ HCl to remove unbound chloride ions. Subsequently, the beads are washed with a 10% (w/w) sodium sulfate solution to countersaturate the exchange sites with $SO_4^=$. The effluent of the sodium sulfate wash is collected and contains liberated chloride ions. This solution is titrated with 1 M silver nitrate using dilute potassium chromate as an indicator.

After titration, the beads are washed thoroughly with distilled water, rinsed with the phosphate-buffered saline solution (PBS), suspended in PBS and autoclaved. This procedure yields hydrated beads of approximately 120–200 μm in diameter, which carry about 2.0 meq of charge capacity per gram of dry, untreated, crosslinked dextran.

EXAMPLE 2

Growth of Anchorage-Dependent Cells With Microcarriers of this Invention Contrasted to Commercially Available Ion Exchange Resin All cells were grown in Dulbecco's Modified Eagle's Medium. For growth of normal diploid fibroblasts, the medium was supplmented to 10% with fetal calf serum. For growth of primary and secondary chicken fibroblasts, the medium was supplemented with 1% chicken serum, 1% calf serum, and 2% tryptose phosphate broth (Difco Laboratories, Detroit, MI). Stocks were passaged on 100-mm plastic dishes (Falcon Plastics, Inc., Oxnard, CA).

Primary chicken embryo fibroblasts were prepared by mincing and sequentially trypsinizing 10-day embryos. Secondary chicken embryo fibroblasts were prepared on the first day of primary confluence by trypsinization. For cells grown in plastic dishes, doubling time was about 20 hours.

Diploid human fibroblasts derived from embryonic lung (HEL299, ATCC #CCL 137) were obtained from the American Type Culture Collection, Rockville, MD. These cells had a doubling time of 19 hours in plastic dishes.

Microcarrier cultures were initiated simply by combining cells and beads in stirred culture. 100-ml culture volumes in 250-ml glass spinner bottles (6.5 cm in diameter) equipped with a 4.5-cm magnetically driven Teflon ®-coated stir bar (Wilbur Scientific, Inc., Boston, MA) were used. Stirring speed was approximately 90 rpm. Cultures were sampled directly, and samples were examined microscopically and photographed. Cells were enumerated by counting nucleii using the modification of the method of Sanford et al. (Sanford, K. K., Earle, W. R., Evans, V. J., Waltz, H. K., and Shannon, J. E. (1951) *J. Natl Cancer Inst.* 11: 773.) as described by van Wezel (van Wezel, A. L. (1973). *Tissue Culture, Methods and Applications.* Kruse, P. F. and Patterson, M. R. (eds.), pp. 372–377, Academic Press, New York).

Beads with attached cells were separated from the culture medium by permitting the beads to settle at 1 g for a few minutes and then aspirating the supernatant. This procedure greatly facilitated and replacement of medium as well as facilitating the separation of cells from microcarriers after trypsinization.

Commercial DEAE Sephadex A-50 was used as microcarrier for the diploid human fibroblasts and compared with carriers synthesized and titrated as described in Example 1. For both bead types, carrier concentration was 2 grams of dry, untreated, crosslinked dextran per liter. The charge capacity of the DEAE Sephadex A-50 was 5.4 meq/g of dry, crosslinked dextran, while that of the newly synthesized beads was 2.0 meq/g. The results are illustrated in FIG. 1.

For this cell type, loss of original inoculum on A-50 microcarriers was marked, while the fibroblasts attach, proliferate, and reach confluence on the microcarriers of this invention in six days. This behavior agrees well with the reported behavior of this cell type on standard plates. As FIG. 1 shows, the final cell density achieved with the new microcarriers at 2 grams dry, crosslinked dextran/liter was $1.2 \times 10^6$ cells/ml.

Figure 2:
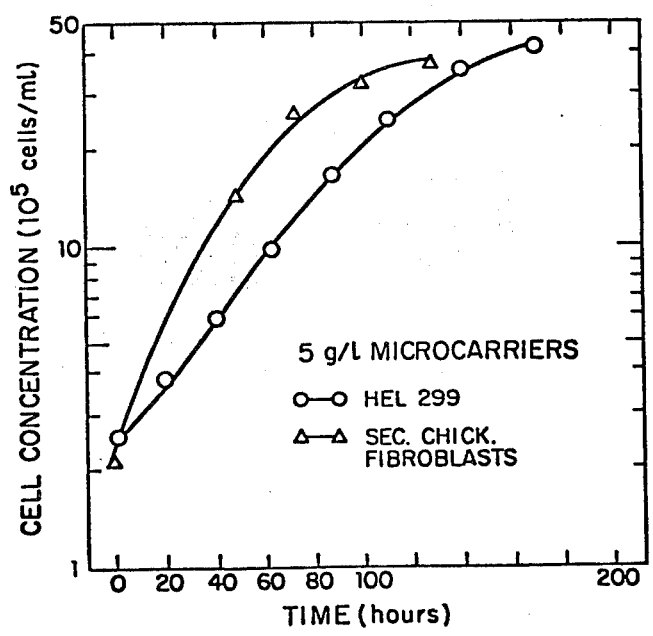
FIG. 2 graphically illustrates the growth characteristics of both normal diploid human embryo lung fibroblast cells (HEL299) and secondary chicken embryo fibroblasts at a microcarrier concentration of 5 grams dry, crosslinked dextran/liter using improved DEAE-treated microcarriers of this invention.

Cultures containing the new carriers demonstrated neither initial cell loss nor any inhibition in reaching confluence. More importantly, the cultures grew normally at higher microcarrier concentrations. In FIG. 2, for example, human fibroblasts and secondary chicken embryo fibroblasts are shown to reach saturation concentrations near $4 \times 10^6$ cells/ml when 5 grams of dry, crosslinked dextran per liter were used with the new carriers having a charge capacity of 2.0 meq/g dextran. As can be seen, even at this relatively high microcarrier concentration, there was no significant loss of inoculum.

Secondary chick embryo fibroblasts were also grown at a microcarrier concentration of 10 grams/liter. With the conditions described above, a saturation concentration of $6 \times 10^6$ cells/ml was achieved; with addition to the medium of an additional 1% fetal calf serum, a saturation concentration of $8 \times 10^6$ cells/ml was achieved. There was no significant loss of cell inoculum.

Primary chick embryo fibroblasts were grown at a microcarrier concentration of 5 and 10 grams/liter and the growth characteristics were similar to those of the secondary chick fibroblasts, although slight inoculum losses were noted and somewhat longer lag times were encountered.

Attempts were also made to grow secondary chick embryo fibroblasts under conditions similar to those used above except that DEAE-Sephadex A-50 microcarriers at concentrations of 1 and 5 grams/liter were used. No cell growth was detected and significant inoculum loss occurred.

EXAMPLE 3

Preparation of Microcarriers with varying amounts of reactants

Batches of microcarriers were prepared by dissolving diethylaminoethylchloride:chloride and sodium hydroxide in 20 ml of distilled water. The solution was then poured over dry Sephadex G-50 beads after which the beads were placed on a reciprocating shaker-water table maintained at 60° C. One set of bead batches were treated with a solution containing 0.01 moles of the amine and 0.015 moles of sodium hydroxide, whereas another set of batches was treated with a solution containing 0.03 moles of the amine and 0.045 moles of sodium hydroxide. The reaction time was varied to produce different meq/g within each batch.

Diploid humam fibroblasts (HEL299) were grown in suspension cultures at a microcarrier concentration of 5.0 grams dry, untreated crosslinked dextran per liter following the procedures of Example 2 using microcarriers having varying meq/gram selected from each batch. Subsequently, productivity ($10^6$ cells grown/liter hour) was calculated and plotted versus meq/gram for each batch of beads produced as above. Curves plotted using data obtained for both sets were similar in shape, having a general bell shape, but the curve from the batches treated with the higher concentration of reactants had a somewhat sharper rise and fall. Carriers yielding excellent cell growth were produced from each batch.

EXAMPLE 4

Preparation of Microcarriers at varying Amine/Alkali Ratios

This example illustrates further changes in the charge capacity which can be obtained by varying DEAE chloride: chloride/NaOH ratios. In this example, the procedures of Example 3 were followed except that a wide range of concentrations of sodium hydroxide was used while maintaining the concentration of the diethylaminoethylchloride:chloride at 0.01 moles per 20 ml. The concentrations used for the sodium hydroxide were 0.01, 0.011, 0.012, 0.013, 0.014, 0.015, 0.02, 0.03, 0.05, 0.75, 0.10 moles per 20 ml.

A plot was made of meq/gram after 1.25 hours at 60° C. versus concentration of sodium hydroxide. It was observed from the plot that concentrations of sodium hydroxide below about 0.01 produced no detectable charge capacity. Charge capacity rose quickly, however, with increases in concentration and reached a maximum of around 2.3 meq/gram dry, crosslinked dextran at a concentration of about 0.014 moles sodium hydroxide. Charge capacity then declined in an almost linear relationship to a value of about 1.1 meq/gram at a sodium hydroxide concentration of about 0.10 moles. Thus, a change in reaction kinetics takes place when the ratio of DEAE Chloride:chloride to sodium hydroxide is varied at a constant concentration of DEAE chloride:chloride and crosslinked dextran.

EXAMPLE 5

Human Interferon Production in Cells grown on improved Microcarriers

The ability of microcarrier grown cells to produce human interferon is described herein. Cells used for the production of human interferon were normal diploid human foreskin fibroblasts, FS-4. These fibroblasts were grown in microcarrier cultures using procedures as in Example 2. Microcarriers prepared and titrated according to Example 1 were used at a concentration of 5 grams of dry, crosslinked dextran/liter. The medium used for culture growth was DMEM supplemented with 10% fetal calf serum.

In 8 to 10 days, cultures ceased growing. At this point, growth medium was removed. Cultures were washed 1-4 times with 100 ml of serum-free DMEM. The cells were then ready for interferon induction. This was accomplished by adding to the cultures 50 ml of serum-free DMEM medium containing 50 µg/ml cyclohexamide, and varying amounts of poly I. poly C inducer. After 4 hours, Actinomycin D was added to the cultures to a final concentration of 1 µg/ml.

Five hours after the onset of induction, inducing medium was decanted and cultures were washed 3–4 times with 100 ml of warm serum-free DMEM. Cultures were replenished with 50 ml of DMEM containing 0.5% human plasma protein. Cultures were incubated under standard conditions for an additional 18 hours. At this time, cultures were decanted, and the decanted medium was assayed for interferon activity. Interferon activity was assayed by determining the 50% level of cell protection for samples and standard solutions, for FS-4 fibroblasts challenged with Vesicular Stomatitis Virus (VSV), Indiana strain. The results of interferon production runs are presented in tabular form below.

| Inducer Concentration (µg/ml) | Cell Concentration During Production (cells/ml) | Interferon (U/$10^6$ cells) |
|---|---|---|
| 4 | $2.0 \times 10^6$ | 39 |
| 5 | $2.6 \times 10^6$ | 378 |
| 25 | $2.6 \times 10^6$ | 886 |
| 50 | $2.0 \times 10^6$ | ~5000 | these data are each from a separate run and are not intended to demonstrate any correlation to inducer concentration.

EXAMPLE 6

Growth of Cells on Improved Microcarriers for The Purpose of Producing Viruses

The ability of microcarrier grown cells to produce a virus is described here. Primary and secondary chicken embryo fibroblasts were grown in microcarrier culture according to the procedure described in Example 2 with the primary cells grown at 10 grams/liter and the secondary at 5 grams/liter microcarrier concentration. To initiate virus production, growth medium was removed, and the cultures were washed twice with 100 ml of serum free DMEM. Infection of cells with Sindbis virus took place in 50 ml of DMEM supplemented with 1% calf serum, 2% tryptose phosphate broth, and enough Sindbis virus to equal an MOI (multiplicity of infection) of 0.05.

The virus was harvested 24 hours after infection, by collecting culture broth, clarifying at low centrifugation, and freezing the supernatant. Virus production was assayed by plaque formation in a field of secondary chicken fibroblasts. The results of infecting these microcarrier cultures were:

| Cell Type | All Concentration For Production (cells/ml) | (PFU/ml) | PFU/cell |
|---|---|---|---|
| Secondary | $4.0 \times 10^6$ | $8.4 \times 10^9$ | 2,100 |
| Primary | $1.4 \times 10^6$ | $2.3 \times 10^{10}$ | 16,000 |
| Primary | $6.0 \times 10^6$ | $2.6 \times 10^{10}$ | 5,000 |

Virus production was also established for the following virus/cell on microcarrier combinations: Polio/WI- 38; Moloney MuLV/Cl-1 mouse and VSV/chick embryo fibroblasts.

EXAMPLE 7

Comparative Growth of Cells in Roller Bottles and with Improved Microcarriers for the Purpose of Producing Murine Leukemia Virus Proviral DNA The reverse-transcribed DNA of Moloney leukemia virus (M-MuLV) after infection of JLS-V9 cells, a mouse bone marrow line, was studied.

One technique involved growing cells in roller bottles. Cells were grown in roller bottle culture, the medium removed, and virus inoculum introduced into the bottles. Shortly thereafter, the cultures were fed with fresh medium, and 8–16 hours later extracted for eventual purification of viral DNA. The cultures were washed with fresh buffer and the cell lysed with a solution containing the detergent sodium dodecylsulfate. Subsequent cooling of the lysate and addition of salt to one molar caused coprecipitation of the detergent with high molecular weight DNA. The low molecular weight DNA remaining in the supernatant could then be deproteinized and concentrated for further analysis.

A 50-roller bottle culture contained about $10^9$ cells. These were infected with about one-liter of viral inoculum titering at $3 \times 10^6$ plaque-forming units per ml. This resulted in a nominal multiplicity of infection of 1–3 and the infected cells yielded 5–20 nanograms of virus-specific DNA.

A simpler procedure was developed employing improved microcarriers according to this invention. A culture containing 10 grams of beads in one liter of growth medium was used. Upon reaching confluence, the $10^9$ cells on the beads were infected by allowing the beads to settle out and replacing the medium with 1 liter of virus inoculum. For extraction, the cells on the beads were washed with buffer and then placed in the SDS containing buffer. After co-precipitation of the high molecular weight DNA with the detergent, the precipitate together with the beads were centrifuged out and a supernatant extracted for further analysis. The yield of viral DNA was comparable to that obtained in roller bottle culture and the labor involved was 5–10% of that required by roller bottle culture.

EXAMPLE 8

Improved Microcarrier Production with Dimethylaminoethyl Charge Groups

A suitable microcarrier was produced by binding an alternate exchange moiety to the dextran matrix utilized in Example 1. Dimethylaminoethyl groups (DMAE) were bound to a dextran matrix by the following procedure: 1 gm of dextran beads (Pharmacia G-50), 50–75 $\mu$m in diameter, dry, was added to 10 ml of distilled water and the beads were allowed to swell. An aqueous solution containing 0.01 moles of dimethylaminoethyl-chloride:chloride (Sigma Chemical Co.) and 0.015 moles of sodium hydroxide was formed in a 10 ml volume. This aqueous solution was added to the swollen dextran beads and this suspension was then agitated vigorously for one hour at 60° C. After reaction, the bead mass was titrated as in Example 1. This reaction binds 1.0 meq of dimethylaminoethyl to the dextran mass. To produce microcarriers of greater degrees of substitution, the above reaction was carried out, and the bead mass washed thoroughly with water. With excess water filtered off, the bead mass was weighed so as to determine the amount of water being retained by the bead mass. To this bead mass was added the appropriate amount of fresh reagents (i.e., DMAE-CL:CL, and NaOH) so that the final concentration of DMAE, and NaOH in these succeeding reaction mixtures were identical to those initially used.

In this manner, a series of microcarriers were prepared at 1.0, 2.0, 2.5 and 3.5 meq DMAE/gm unreacted dextran. Cells (HEL 299) were grown in microcarrier culture (5 gm/l) with these microcarriers according to the procedures in Example 2. The results are tabulated in the following table:

| Degree of Substitution (meq/gm) | Cell Spreading | Net Growth |
|---|---|---|
| 1.0 | − | − |
| 2.0 | − | − |
| 2.5 | + | + |
| 3.2 | + | − |

As expected, cell growth is related to the degree of substitution with charge carrying groups. At too high a degree of substitution, no cell growth occurs, although attachment and spreading takes place. At too low a degree of substitution, cell adhesion to the surface is not sufficient to allow proper spreading and growth.

EXAMPLE 9

Improved Microcarriers Having Positively Charged Phosphonium Groups

Improved microcarriers were also prepared using non-amine exchange groups as follows. One gram of dry dextran beads were prepared and swollen with water as in Example 1. To the swollen beads were added 5 ml of a saturated aqueous solution of triethyl-(ethyl-bromide)-phosphonium (TEP),

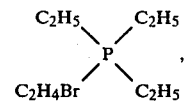

and 5 ml of a 3 molar solution of sodium hydroxide. This slurry was reacted at 65° C. A series of microcarriers were prepared at 1.1, 1.7 and 2.9 meq/gm. Th microcarriers at 1.1 meq/gm were prepared by reaction at the above conditions for 4 minutes. The 1.7 meq/gm microcarriers was reacted for 1 hour, and the 2.9 meq/gm microcarriers were reacted successively 3 times as described in Example 7. A microcarrier cell culture at 5 gm/liter was established for each of these carriers with a continuous cell type, JLS-V9 and compared to this cell's growth on improved DEAE-microcarriers prepared as in Example 3. The results are tabulated in the following table.

| meq/gram | DEAE Cell Attachment and Spreading | Net Growth |
|---|---|---|
| 0.9 | + | + |
| 1.7 | + | + |
| 3.8 | + | − |
| TEP | | |
| 1.1 | + | + |
| 1.7 | + | + |

| | | |
|---|---|---|
| 2.9 | + | − |

It will be recognized by those skilled in the art that there are certain equivalents to the specific techniques, materials, etc., described herein, and these are considered to be part of this invention and are intended to be covered by the following claims. Additionally, while most of the description herein has been limited to the use of the improved microcarriers for growth of anchorage-dependent cells, they can also be used, of course, for the growth of other cell types.

What is claimed is:

1. In a method of growing anchorage-dependent cells in microcarrier culture, the improvement of employing microcarriers having an amount of positively charged chemical moieties thereon adjusted to provide an exchange capacity which allows good growth of said cells, said exchange capacity being within the range of between about 0.1 and about 4.5 meq/gram of dry, untreated microcarriers.

2. In the method of claim 1, the improvement wherein said microcarriers comprise crosslinked dextran beads.

3. In the method of claim 2, the improvement wherein the positively charged chemical moieties on said crosslinked dextran beads comprise tertiary or quaternary amine groups.

4. In the method of claim 3, the improvement wherein said exchange capacity is within the range of from about 1 to about 2.8 meq/gram of dry, untreated crosslinked dextran.

5. In the method of claim 4, the improvement wherein the positively charged chemical moieties on said crosslinked dextran beads comprise diethylaminoethyl groups.

6. In the method of claim 5, the improvement wherein said dry, crosslinked beads have a diameter of approximately 75 μm in their dry state.

7. A method of growing anchorage-dependent cells, comprising:
   a. forming a suspension in cell culture medium of positively charged microcarriers having their charge capacity adjusted to a value which supports good growth of cells, said charge capacity being within the range of from about 0.1 to about 4.5 meq/gram of dry, untreated microcarriers;
   b. inoculating cells into said suspension of microcarriers to form a cell culture; and,
   c. maintaining said cell culture under cell growth conditions.

8. A method of claim 7 wherein said microcarriers comprise crosslinked dextran beads having tertiary or quaternary amine groups thereon.

9. A method of claim 7 wherein said microcarriers comprise crosslinked dextran beads having diethylaminoethyl groups thereon.

10. A method of claim 9 wherein said microcarriers have a charge capacity within the range of between about 1 and about 2.8 meq/gram of dry, untreated crosslinked dextran.

11. A method of claim 10 wherein said microcarriers have an average diameter of about 75 μm.

12. In the method of growing anchorage-dependent cells including forming a suspension in cell culture medium of microcarriers comprising crosslinked dextran beads, inoculating cells into said suspension to form a cell culture and maintaining said cell culture under cell growth conditions:

The improvement of pre-treating said crosslinked dextran beads by reacting them in an aqueous solution of a tertiary or quaternary amine and a base under conditions sufficient to provide a positive charge capacity on said beads which is suitable for exponential growth of said anchorage-dependent cells, said charge capacity being within the range between about 0.1 and about 4.5 meq/gram of dry, untreated microcarriers.

13. A method for producing anchorage-dependent cell growth by-products comprising:
   a. forming a suspension of positively-charged microcarriers having a charge capacity sufficient for good growth of anchorage dependent cells in a suitable cell culture medium, said charge capacity being between about 0.1 and about 4.5 meq/gram of dry, untreated microcarriers;
   b. inoculating said culture with anchorage-dependent cells to form a cell culture;
   c. maintaining said cell culture under conditions conducive to the production of cell growth by-products; and,
   d. harvesting said cell growth by-products.

14. A method of claim 13 wherein said cell growth by-product is a virus.

15. A method of claim 13 wherein said cell growth by-product is a hormone.

16. A method of claim 13 wherein said cell growth by-product is interferon.

17. A method of claim 13 wherein said microcarriers comprise a reaction product of crosslinked dextran beads and an aqueous solution of a tertiary or quaternary amine and a base.

18. A method of claim 13 wherein said microcarriers comprise crosslinked dextran beads having diethylaminoethyl groups thereon.

19. A method of claim 18 wherein said charge capacity is in the range of from about 1 to about 2.8 meq/grams of dry, untreated microcarriers.

20. A method of claim 19 wherein said reaction product comprises hydrated beads having an average diameter of about 120–200 μm.

* * * * *